United States Patent [19]

Mason, Jr.

[11] 4,257,558

[45] Mar. 24, 1981

[54] CONTENT INDICATING DISPENSER UTILIZING DISPLACEMENT OF THE CENTER OF GRAVITY OF THE CONTENTS AND THE DISPENSER TO PROVIDE AN INDICATION OF THE QUANTITY OF CONTENTS REMAINING IN THE DISPENSER

[76] Inventor: Stanley I. Mason, Jr., 61 River Rd., Weston, Conn. 06880

[21] Appl. No.: 41,713

[22] Filed: May 23, 1979

[51] Int. Cl.$^3$ .............................................. A61L 9/04
[52] U.S. Cl. ........................................ 239/57; 220/70; 239/60
[58] Field of Search ...................... 239/34, 35, 47, 43, 239/46, 49, 51.5, 55, 56, 58, 57; 222/463; D23/148, 150; 116/227; 220/70

[56] References Cited

U.S. PATENT DOCUMENTS

| | | | |
|---|---|---|---|
| 2,707,930 | 5/1955 | Miles | 239/35 X |
| 3,239,145 | 3/1966 | Russo | 239/54 X |
| 3,805,995 | 4/1974 | Lebel et al. | 116/227 X |
| 4,040,568 | 8/1977 | Mason et al. | 239/57 |

*Primary Examiner*—Robert B. Reeves
*Assistant Examiner*—Gene A. Church
*Attorney, Agent, or Firm*—Parmelee, Johnson, Bollinger & Bramblett

[57] ABSTRACT

A dispenser is designed to provide a visual indication whenever the remaining quantity of contents to be dispensed is less than a predetermined amount. The dispenser is particularly suitable for dispensing vaporizable material such as room deodorants or insecticides. The dispenser is made of lightweight plastic material and has internal space to hold the vaporizable material and air openings for permitting the material to slowly dissipate into the surroudning environment. It is designed, however, to be physically unstable in the absence of a predetermined weight of the vaporizable material. Thus, when the dispenser is full, or partially full, it will stand up, but when the vaporizable material is almost depleted, that is, below the predetermined weight, the dispenser will not stand and falls over, indicating to the user that either a refill is needed or the dispenser must be replaced. The dispenser includes a housing and a supporting base. The housing contains the vaporizable material to be dispensed and has air outlets through which the vapors can pass. The structure of the housing is such that when the weight of the material contained therein is less than a predetermined weight, the center of gravity of the housing and the contents is not above the supporting base, but when the weight of the contents is greater than the predetermined value, the center of gravity of the housing and the contents is shifted above the supporting base.

6 Claims, 11 Drawing Figures

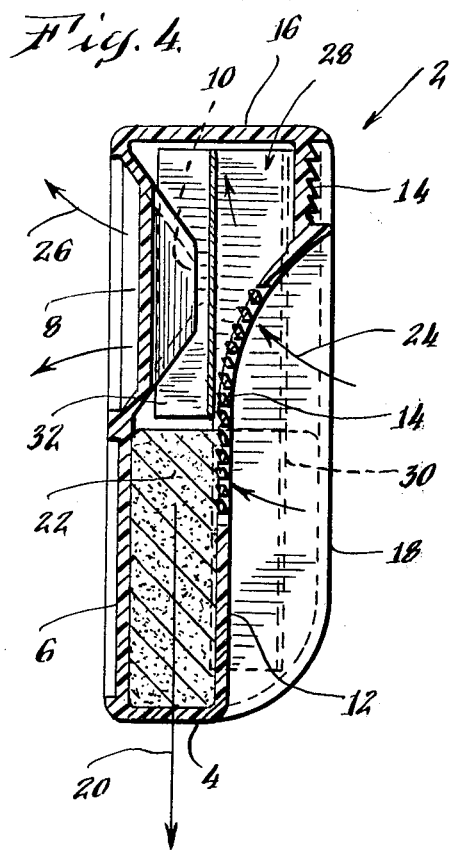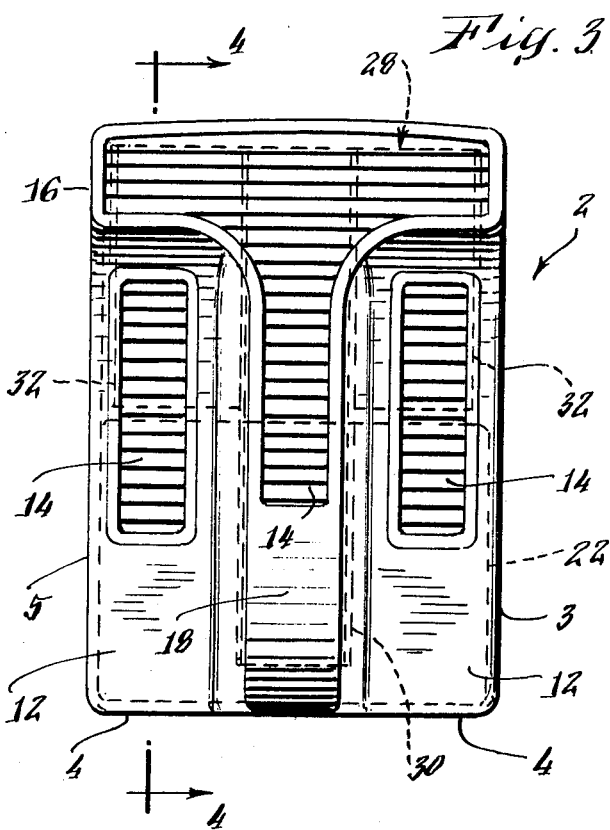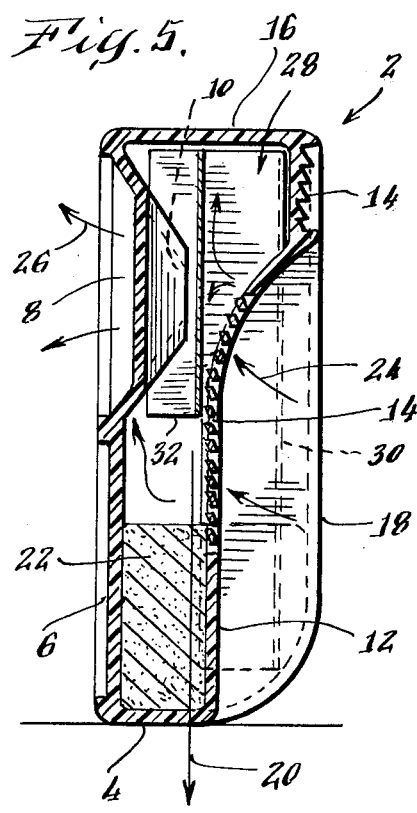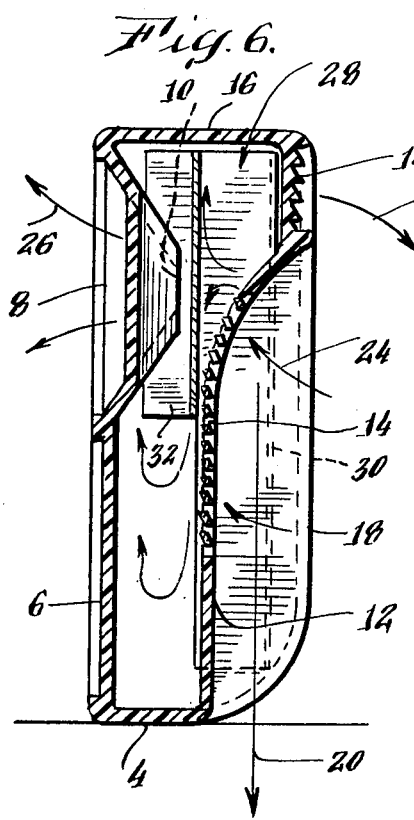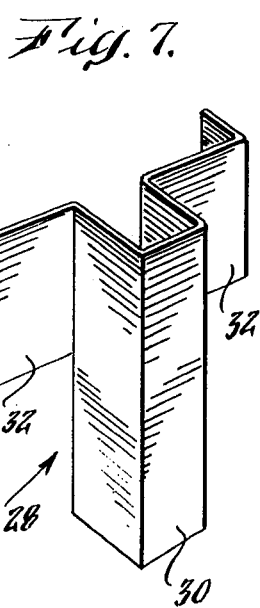

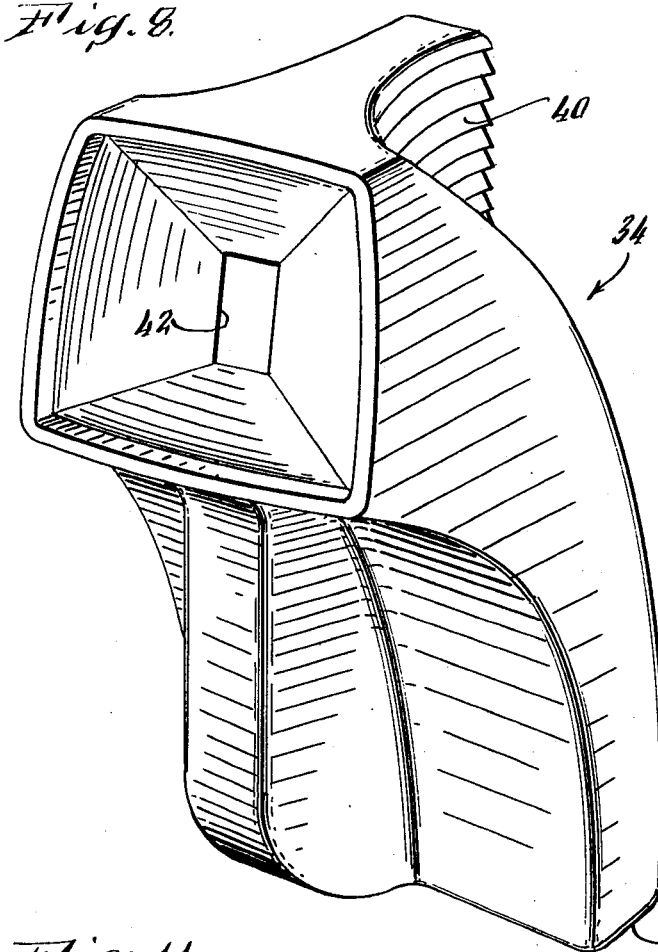
Fig. 8.
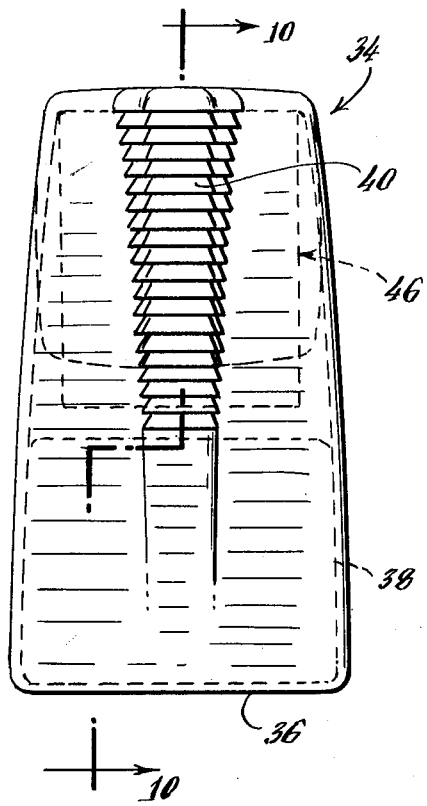
Fig. 9.
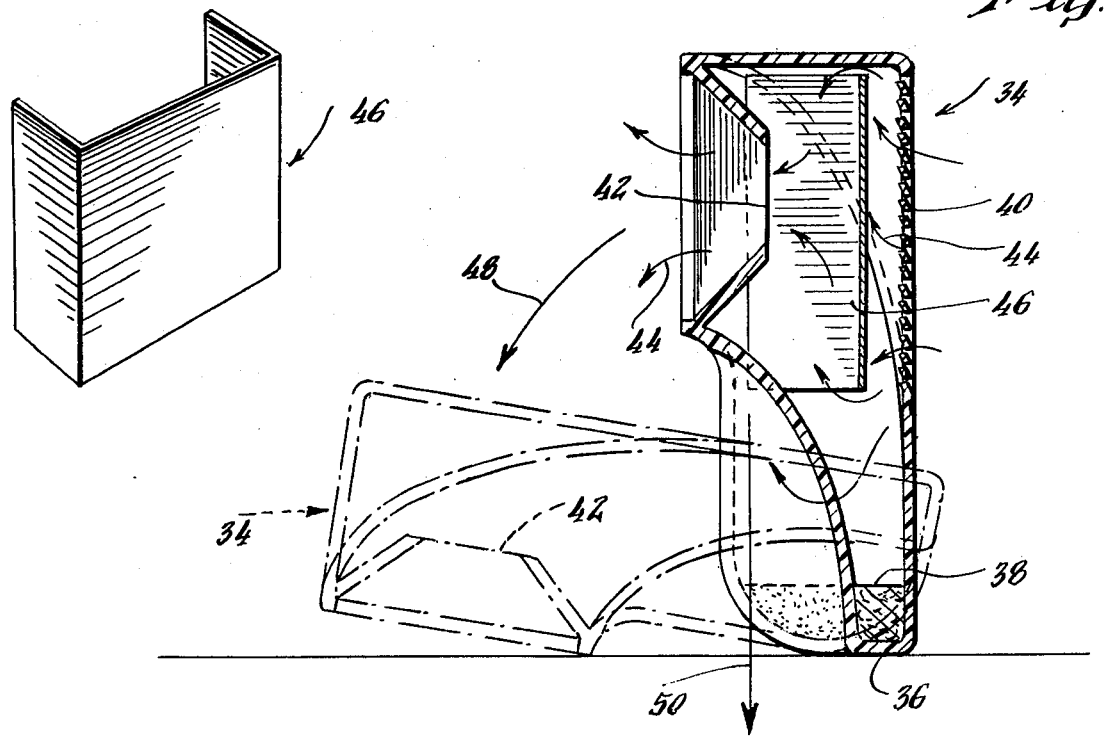
Fig. 11.
Fig. 10.

CONTENT INDICATING DISPENSER UTILIZING DISPLACEMENT OF THE CENTER OF GRAVITY OF THE CONTENTS AND THE DISPENSER TO PROVIDE AN INDICATION OF THE QUANTITY OF CONTENTS REMAINING IN THE DISPENSER

BACKGROUND OF THE INVENTION

Various types of dispensers exist for releasing vaporizable material into the surrounding environment. These dispensers are commonly used to dispense materials such as deodorants, room fresheners, or insecticides.

The known dispensers do not provide any type of definitive indication when the contents have been totally expended. Consequently, it is not uncommon for an empty dispenser to go unnoticed for a long period of time.

Thus, users of the known dispensers have had to rely on rough estimates when to replace the vaporizable material. This can result in a large time lag between the time when the material has actually been expended until the time that this fact is discovered by the user, or in premature replacement.

The present invention provides a dispenser adapted to release vaporizable material into the ambient environment which provides an immediate and unambiguous visual indication that the quantity of the material to be dispensed has fallen below a predetermined level and is nearly or totally expended. The dispenser is designed so that it is capable of standing upright in a vertical position on a base only when the weight of its contents is above a predetermined value. However, the center of gravity of the contents and the dispenser shifts so that the dispenser is unstable in its vertical upright position when the weight of its contents is below the predetermined value. The unstable dispenser falls to its side, and the fallen container provides a user with an unmistakable visual indication, at a glance, that the contents within the container have been depleted or are close to depletion, thus requiring replacement.

SUMMARY OF THE INVENTION

The present invention relates to a dispenser for dispensing material and for storing a portion of such material which has not been dispensed. It is particularly adapted to releasing a vaporizable material, as for example a room freshener, a deodorant, or an insecticide, and is designed to provide a visual indication when the material within the dispenser is depleted below a predetermined quantity.

The dispenser includes a housing and an associated supporting base for supporting the housing in a vertical upright position. The material to be dispensed is contained within the housing, which includes openings or ports on both sides for conducting air flow through the housing, and thus releasing vapors from the housing into the ambient environment.

The housing is designed so that its center of gravity is not located above the supporting base when there is either no material within the housing or the contents are less than a predetermined weight. In such condition, the dispenser is unstable in a vertical position and will fall over to one side. However, when the weight of the contents within the housing is greater than the predetermined weight, the center of gravity of the housing and the material is located above the supporting base. Consequently, the dispenser is stable and will stand upright on its supporting base.

Accordingly, the new dispenser provides an easily perceivable visual indication when its contents have been depleted below the predetermined level. A glance at the fallen dispenser immediately indicates that its contents are below the predetermined quantity and refill or replacement is, or imminently will be, required.

BRIEF DESCRIPTION OF THE DRAWINGS

FIG. 3 is a rear elevational view of the dispenser.

FIGS. 4-6 are sections taken along arrows 4—4 of FIG. 3 showing the dispenser holding various amounts of material to be dispensed.

FIG. 7 is a perspective view of an air flow control device used in the first embodiment of the dispenser.

FIG. 8 is a front perspective view of a second embodiment of a content indicating container constructed in accordance with the present invention.

FIG. 9 is a rear elevational view of the embodiment shown by FIG. 8.

FIG. 10 is a sectional view taken along arrows 10—10 of FIG. 9. A fallen dispenser is also shown in phantom.

FIG. 11 is a perspective view of a flow control device used in the second embodiment of the dispenser.

DESCRIPTION OF THE PREFERRED EMBODIMENTS

FIGS. 1-11 of the drawings illustrate two embodiments of an automatic content indicating dispenser for dispensing a material, in accordance with the present invention. Each of these embodiments is designed so that it is physically stable and capable of standing upright when greater than a predetermined weight of contents is within the dispenser, but is unstable and will fall to one side when it is holding less than the predetermined weight of contents. Consequently, a determination of whether the cotnents are above or below the predetermined weight can be made by observing whether the dispenser is upright or has fallen. By designing the dispenser such that the predetermined value of contents is a relatively small quantity, a fallen dispenser will provide a visual indication that the contents within the dispenser have already been or are nearly totally expended.

Figure 1:
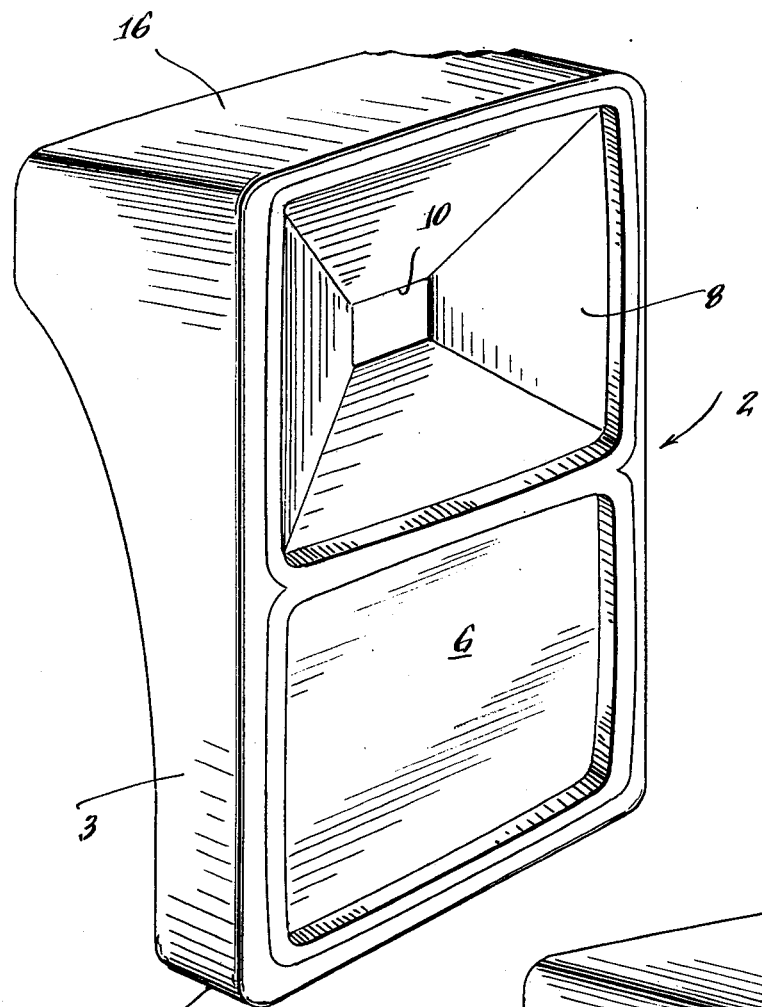
FIG. 1 is a front perspective view of one embodiment of a content indicating dispenser constructed in accordance with the present invention.

Referring to FIGS. 1-7, one embodiment of the dispenser comprises a housing indicated generally by the numeral 2 and a supporting base indicated by numeral 4. As shown in FIG. 1, the housing is supported in a vertical upright position on its supporting base, which is formed integral with the housing.

The front surface of the housing, indicated by numeral 6, has an upper recessed portion 8 and an air outlet port 10 defined at the approximate center of the recessed portion. The rear surface of the housing, indicated by numeral 12, includes an air inlet port, which, in this embodiment, is shown as louvers 14.

Figure 2:
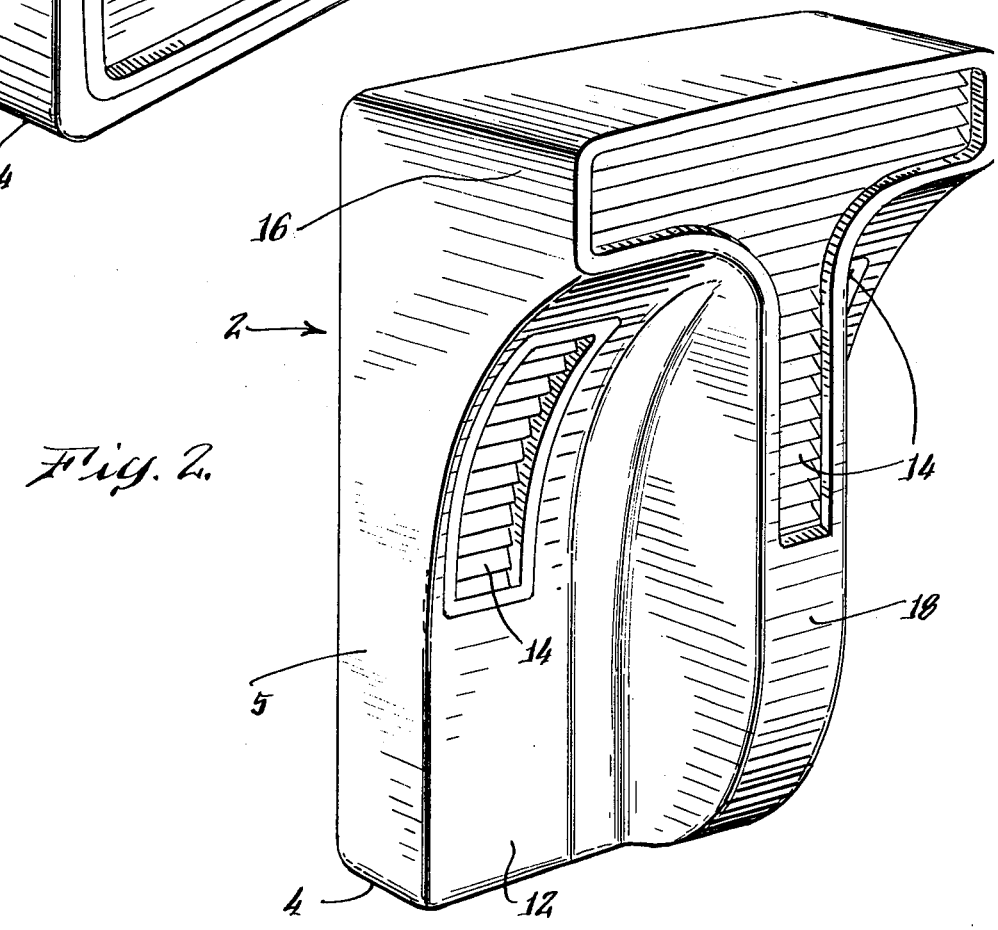
FIG. 2 is a rear perspective view of the embodiment illustrated by FIG. 1.

As is best shown by FIGS. 1 and 2, the width of the sides 3 and 5 of the housing 2 increase towards the top of the housing, defining a rearwardly extending projection 16. This projection extends beyond the periphery of the supporting base 4 beneath it. The rear surface of the housing also defines a vertical column 18 which intersects with the projection 16 to form a rearwardly extending "T" shaped projection, as is shown by FIG. 2. This column is rounded towards its bottom.

The housing itself is at least partially hollow and can be formed from an inexpensive, lightweight material, such as plastic. The internal space defind within the housing serves to hold a vaporizable material to be dispensed.

Operation of the new dispenser is best described with reference to FIGS. 3 to 6. As schematically shown in FIG. 6, the center of gravity (indicated by arrow 20) of an unfilled dispenser is not vertically aligned above the supporting base, but extends beyond the area of the supporting base. This results from the design of the dispenser which is constructed so that a substantial portion of the weight of the housing extends rearwardly of the supporting base. In the presently described embodiment, such weight distribution of the housing results from the upper rearwardly extending projection 16 and the rear vertical projection 18, both of which extend beyond the periphery of the supporting base 4. Consequently, the empty dispenser falls in the direction of arrow 9 of FIG. 6 towards its rear surface.

FIG. 4 illustrates a schematic view of a dispenser which is partially filled with vaporizable material 22. Due to gravitational forces, the weight of the vaporizable material is concentrated in the lower portion of the housing directly above the supporting base 4. Material 22 exceeds the predetermined amount necessary for stability. As shown by arrow 20, the center of gravity of the dispenser and the material to be dispensed is directly above the supporting base 4, and, as a result, the dispenser is stable and will stand on its supporting base in an upright vertical position. In effect, the concentration of the weight of the material in the lower portion of the housing above the supporting base counterbalances the rearwardly concentrated weight of the housing itself (due to projection 16 and column 18) to shift the center of gravity of the overall system (consisting of the housing and the material) to above the supporting base.

FIG. 5 illustrates a third schematic view of the dispenser which is also partially filled with vaporizable material 22 to be dispensed. The weight of material in the housing is less than that shown in FIG. 4, and the center of gravity (arrow 20) of the dispenser and the material is shown to be proximate to the rear edge of the supporting base 4. Any further reduction in the quantity (and, consequently the weight) of the material will shift the weight distribution of the dispenser and the material so that their combined center of gravity will no longer be directly about a portion of the supporting base. As previously discussed with reference to FIG. 6, this will result in the dispenser being vertically unstable, and the dispenser will fall towards its rear surface.

It now becomes apparent from the above discussion that the new dispenser is designed to use a predetermined weight of its vaporizable contents to control the vertical stability of the dispenser. If the quantity (and weight) of the material is greater than that shown in FIG. 5, the weight distribution of the dispenser and material is concentrated directly above the supporting base 4 and thus provides vertical stability. However, if the quantity, and thus the weight, of the material to be dispensed is less than the predetermined amount shown in FIG. 5, the weight distribution of the housing and the material will not be directly above the supporting base, but their combined center of gravity will be towards the rear of the supporting base, causing the dispenser to fall.

As best shown by FIG. 2, the bottom of the rearwardly projecting column 18 is rounded to facilitate the rear tipping of the dispenser when the center of gravity of the dispenser and its contents are shifted rearwardly of the supporting base 4.

Accordingly, a vertically standing dispenser provides a visual indication that the quantity of material remaining within the housing is greater than a predetermined quantity, while a fallen dispenser indicates that the quantity of material within the housing is less than a predetermined quantity. The specific predetermined quantity is determined by the construction of the dispenser. For example, the predetermined quantity of material required to provide the dispenser with vertical stability can be increased by shifting the concentration of weight of the housing further away from the supporting base, as for example, increasing the size of the projection 16. In any event, ways of constructing the housing to adjust the level of this predetermined quantity will be apparent to those skilled in the art.

The housing should be constructed so that the level of the predetermined weight of material is a relatively small portion of the initial weight of material in the housing, such as 25%. In this way, a fallen container will indicate not only that the quantity of material is below the predetermined level, but will also indicate that the quantity of material remaining is near depletion.

In operation, the dispenser, which initially contains a weight of vaporizable material greater than the predetermined weight, is stood upright on its base in a location to be treated with the vaporizable material. Ambient air currents at that location enter the housing through the rear louvers 14. The entering air circulates around the vaporizable material in the housing and carries away a portion of that material in vapor form. The air and the vapor from the material normally leave the housing through the front outlet port 10. The circulation of air through the housing are shown by arrows 24 and 26 in FIGS. 4–6. Because vaporizable material is carried from the housing by the flowing air, the weight of such material remaining in the housing is slowly, but continually diminished. As previously discussed, when the weight of material remaining in the housing drops below a predetermined level, the center of gravity of the dispenser and the remaining material is relocated to a position not directly above the supporting base of the dispenser but to its rear. The dispenser is now vertically unstable and will fall rearwardly, the fallen dispenser indicating that the material remaining therein is almost depleted.

Although the embodiment of the dispenser described herein discloses that the opening 10 on the front of the dispenser is the air outlet and the louvers 14 on the rear end of the housing is the air inlet, the functions of these two openings are reversible. That is, it is possible for air to flow inwardly into the housing through the front opening 10 and out of the housing through the rear louvers 14. In practice, the actual direction of air flow through the housing will be determined by the flow of the ambient air currents surrounding the dispenser.

The dispenser also includes an aerodynamic shield 28 which is best illustrated by FIG. 7. The shield includes a center member 30 and two outwardly extending folded arms 32. As shown in FIGS. 4–6, the shield is placed within the housing 2 of the dispenser and is interposed between the inlet and outlet openings of the dispenser. Consequently the shield acts as a baffle to deflect inwardly flowing air towards the vaporizable material in the lower portion of the housing. That is, the shield obstructs inflowing air streams and causes them to flow around the shield, causing turbulence within the housing. Turbulent air flow within the housing proximate to the vaporizable material enhances the quantity of vaporizable material carried off by the air circulating through and inside of the housing. The baffle or shield 28 prevents air from flowing in and out of the housing without passing through an area having a relatively large concentration of vaporizable material.

The dispenser is preferably made from a lightweight material, as for example, plastic, and consequently can be disposed of after its contents are expended. In the alternative, conventional means (not shown), as for example, an opening on the housing and a door pivotally mounted above the opening, can be provided for refilling the dispenser for re-use after the original material has been expended. Additionally, the dispenser can be provided with a removable top or cap (not shown) which can be removed to refill an empty dispenser.

Referring now to FIGS. 8 to 11, a second embodiment of the dispenser is shown. This embodiment which is similar to the previously discussed first embodiment, includes a housing 34 for holding vaporizable material 38, supported in a vertical position on a supporting base 36. Louvers 40 are defined at the rear of the housing and outlet port 42 is defined at the front of the housing. In this embodiment, the air flow through the housing (as shown by arrows 44) is into the rear louvers and out of the front outlet port. A "U" shaped aerodynamic shield or baffle 46, as shown by FIG. 11, is placed within the upper portion of the housing between the louvers and the outlet port to deflect inflowing air towards the vaporizable material in the lower portion of the housing.

The principal of operation of this embodiment is the same as that of the previously discussed first embodiment, and will not be repeated. The basic difference between the first and second embodiments is that the second embodiment is designed so that the weight of its empty housing is concentrated in front of the supporting base and not behind it. Accordingly, the empty dispenser will fall forward. Likewise, the dispenser will fall forward, as illustrated by arrow 48 in FIG. 10, when the weight of material to be dispensed from the housing drops below its predetermined weight and the center of gravity of the dispenser and its contents is not directly above the supporting base 36, as shown by arrow 50 of FIG. 10.

The two embodiments of the dispenser illustrated herein advantageously provide a user with a visual indication when the contents to be dispensed have fallen below a predetermined value. Modifications of the disclosed embodiments will be apparent to those skilled in the art. Accordingly, the description of the two embodiments disclosed herein are intended to be illustrative only, and not restrictive of the scope of the invention, that scope being defined by the following claims and all equivalents thereto.

I claim:

1. A content indicating dispenser for vaporizable material such as room deodorants and insecticides, said dispenser including:

a housing for holding said vaporizable material, said housing defining at least one chamber therein for receiving said vaporizable material, and said housing having at least one discharge opening communicating with said at least one chamber through which said vaporizable material is released from said chamber and into the environment surrounding said dispenser, a supporting base affixed to the bottom of said housing for supporting said housing in a vertical position on said supporting base, said housing being so shaped and dimensioned relative to said supporting base that (1) the center of gravity of said housing and said vaporizable material within said housing is not substantially above said supporting base and said dispenser is physically unstable standing upright on its supporting base and will topple in the absence of a predetermined weight of said vaporizable material within said housing and (2) said center of gravity of said housing and said vaporizable material within said housing is substantially above said supporting base when said vaporizable material exceeds said predetermined weight, said housing including an integrally formed projection extending therefrom proximate the top of said housing, said projection extending beyond the periphery of said supporting base and being of such weight that the center of gravity of said housing is not substantially above said supporting base when no vaporizable material is within said housing, whereby the weight of said vaporizable material controls the stability of said dispenser such that said dispenser is vertically stable on its supporting base only when at least said predetermined weight of said vaporizable material is within said housing, and whereby a vertically upright dispenser indicates that the quantity of vaporizable material within said housing is at least equal to said predetermined weight, and a toppled dispenser indicates that the vaporizable material within said housing is less than said predetermined weight.

2. A content indicating dispenser for vaporizable material such as room deodorants and insecticides, said dispenser including:

a housing for holding said vaporizable material, said housing including at least one chamber for receiving said vaporizable material defined within said housing, and said housing having at least one discharge opening communicating with said at least one chamber through which said vaporizable material is released from said chamber and into the environment surrounding said dispenser, a supporting base affixed to the bottom of said housing for supporting said housing in a vertical position on said supporting base, said housing including a projection extending from the top thereof and beyond the periphery of said supporting base, the weight of said projection being such that the center of gravity of said housing and said vaporizable material within said housing is not substantially above said supporting base and said dispenser is unstable on its supporting base and will topple in the absence of a predetermined weight of vaporizable material within said housing, said center of gravity of said housing and said vaporizable material being substantially above said supporting base only if at least said predetermined weight of said vaporizable material is within said housing, the weight of said vaporizable material controlling the stability of said dispenser such that said dispenser is vertically stable on its supporting base only when at least said predetermined weight of said vaporizable material is within said housing, whereby a vertically upright dispenser indicates that the quantity of vaporizable material within said housing is at least equal to said predetermined weight, and a toppled dispenser indicates that the vaporizable material within said housing is less than said predetermined weight.

3. A dispenser as claimed in claim 2 wherein said supporting base is formed integral with the bottom of said housing.

4. A dispenser as claimed in claim 3 including an air inlet opening defined on said housing and opposite to said at least one discharge opening such that air currents entering said air inlet opening pass through said housing and are discharged through said discharge opening, wherein a portion of said vaporizable material within said housing is discharged in vapor form through said discharge opening together with said air currents.

5. A dispenser as claimed in claim 4 including a baffle mounted within said housing and interposed between said air inlet opening and said discharge opening, said baffle being configured to direct the flow of air entering said inlet opening towards said vaporizable material within said housing.

6. A content indicating dispenser for vaporizable material such as room deodorants and insecticides, said dispenser including:

a housing for holding said vaporizable material, said housing defining at least one chamber therein for receiving said vaporizable material, and said housing having at least one discharge opening communicating with said at least one chamber through which said vaporizable material is released from said chamber and into the environment surrounding said dispenser, a supporting base affixed to the bottom of said housing for supporting said housing in a vertical position on said supporting base, said housing being so shaped and dimensioned relative to said supporting base that (1) the center of gravity of said housing and said vaporizable material within said housing is not substantially above said supporting base and said dispenser is physically unstable standing upright on its supporting base and will topple in the absence of a predetermined weight of said vaporizable material within said housing and (2) said center of gravity of said housing and said vaporizable material within said housing is substantially above said supporting base when said vaporizable material exceeds said predetermined weight, said housing including an integrally formed projection extending therefrom proximate the top of said housing, said projection extending beyond the periphery of said supporting base and being of such weight that the center of gravity of said housing and said vaporizable material contained therein is not substantially above said supporting base when the weight of said vaporizable material is less than said predetermined weight, whereby the weight of said vaporizable material controls the stability of said dispenser such that said dispenser is vertically stable on its supporting base only when at least said predetermined weight of said vaporizable material is within said housing, and whereby a vertically upright dispenser indicates that the quantity of vaporizable material within said housing is at least equal to said predetermined weight, and a toppled dispenser indicates that the vaporizable material within said housing is less than said predetermined weight.

* * * * *